United States Patent
Kitajima et al.

(10) Patent No.: US 6,915,232 B2
(45) Date of Patent: Jul. 5, 2005

(54) FILM THICKNESS MEASURING METHOD, RELATIVE DIELECTRIC CONSTANT MEASURING METHOD, FILM THICKNESS MEASURING APPARATUS, AND RELATIVE DIELECTRIC CONSTANT MEASURING APPARATUS

(75) Inventors: Toshikazu Kitajima, Kyoto (JP); Motohiro Kono, Kyoto (JP)

(73) Assignee: Dainippon Screen Mfg. Co., Ltd. (JP)

( * ) Notice: Subject to any disclaimer, the term of this patent is extended or adjusted under 35 U.S.C. 154(b) by 0 days.

(21) Appl. No.: 10/624,871

(22) Filed: Jul. 21, 2003

(65) Prior Publication Data

US 2004/0019442 A1 Jan. 29, 2004

(30) Foreign Application Priority Data

Jul. 22, 2002 (JP) ........................... 2002-212884
Jun. 16, 2003 (JP) ........................... 2003-171087

(51) Int. Cl.[7] ............................................. G01B 11/02
(52) U.S. Cl. ........................................ 702/171; 324/445
(58) Field of Search .......................... 702/170; 324/455, 324/765, 71.5

(56) References Cited

U.S. PATENT DOCUMENTS 5,475,319 A * 12/1995 Hirae et al. .................. 324/765
5,485,091 A * 1/1996 Verkuil ......................... 324/455
6,278,267 B1 * 8/2001 Okada et al. ................ 324/71.5

FOREIGN PATENT DOCUMENTS

JP      6-349920      12/1994

* cited by examiner

Primary Examiner—John Barlow
Assistant Examiner—Xiuqin Sun
(74) Attorney, Agent, or Firm—Ostrolenk, Faber, Gerb & Soffen, LLP

(57) ABSTRACT

A non-contact method of measuring the thickness of an insulator film on a semiconductor substrate includes: (i) charging the insulator film surface in a non-contact manner; (ii) obtaining a first flat band voltage by conducting, prior to the charging processing step, a C-V measurement on the semiconductor substrate; obtaining a second flat band voltage by conducting, after the charging processing step, a C-V measurement on the semiconductor substrate; and calculating, based on a difference between the first and second flat band voltages, the charge amount given to the insulator film surface by the charging processing step; (iii) then measuring the insulator film surface potential and (iv) calculating the insulator film thickness based on the charge amount measured at the charge amount measuring step and on the surface potential measured at the surface potential measuring step.

11 Claims, 4 Drawing Sheets

FILM THICKNESS MEASURING METHOD, RELATIVE DIELECTRIC CONSTANT MEASURING METHOD, FILM THICKNESS MEASURING APPARATUS, AND RELATIVE DIELECTRIC CONSTANT MEASURING APPARATUS

BACKGROUND OF THE INVENTION

1. Field of the Invention

The present invention relates to a film thickness measuring method, a relative dielectric constant measuring method, a film thickness measuring apparatus, and a relative dielectric constant measuring apparatus in each of which an insulator film formed on a surface of a semiconductor substrate is an object to be measured.

2. Description of Related Art

A semiconductor device is to be produced by forming, on a semiconductor substrate, a variety of films including an insulator film. The characteristics of the insulator film have a great influence on the characteristics of the semiconductor device. It is therefore inevitable to evaluate the characteristics of the insulator film during the semiconductor device production processing.

With the progress of semiconductor device integration technology, the type and thickness of an insulator film have undergone a change. This has consequently changed the insulator film evaluation method. For example, there have been instances where an optical method (e.g., ellipsometry) is used as a method of measuring the thickness of an insulator film. Such an optical method could not always achieve an accurate measurement under the influence of an organic substance attached to the insulator film surface. Therefore, attention is now placed on an electric film thickness measuring method directly related to the device operation.

With the progress of the multilayer-film technology of forming wirings as sandwiching an interlayer insulator film, the relative dielectric constant of the insulator film becomes an important parameter. It is therefore required to measure more accurately the relative dielectric constant of the insulator film.

In the insulator film, the film thickness can be obtained when the surface charge amount, the surface potential and the relative dielectric constant are known. The relative dielectric constant can be obtained when the surface charge amount, the surface potential and the film thickness are known. Accordingly, when either the film thickness or the relative dielectric constant is known in addition to the surface charge amount and the surface potential, the other can be obtained.

In measurement of the film thickness or relative dielectric constant of an insulator film, there is a measuring method in which electrodes are formed on the surface of the insulator film. However, this method is not desirable because this is a destructive test and includes a number of processing steps. There is also a measuring method using mercury as electrodes. However, the mercury is detrimental to the human body and is therefore hard to deal with. Further, when the electrodes are formed on the surface of the insulator film, this involves the likelihood that an electric current leaks through the insulator film at the time of measurement, making the measurement inaccurate.

It is therefore desired to establish a method of measuring, in a non-contact manner, the thickness or relative dielectric constant of an insulator film. Examples of such a method include a method of measuring the surface charge amount and surface potential of an insulator film at the time when the insulator film surface is electrically charged by corona discharge, and of obtaining, based on the values thus measured, the thickness or relative dielectric constant of the insulator film.

However, the surface charge amount of the insulator film could not conventionally been measured directly. As a matter of fact, the charge given to the insulator film at the time of corona discharge has been measured by a Coulomb meter, or the electric current flowing to the semiconductor substrate has been measured. Based on the values thus measured, the insulator film surface charge amount has been obtained indirectly.

With the progress of the semiconductor technology, the pattern is increasingly miniaturized. Accordingly, the gate oxide layer becomes thinner and the interlayer insulator film is lowered in dielectric constant. Further, there exists an electric current which leaks through the insulator film. Accordingly, the insulator film surface charge amount could not accurately be obtained by the indirect measuring method above-mentioned. Thus, the thickness or relative dielectric constant of an insulator film could not be accurately measured.

SUMMARY OF THE INVENTION

It is an object of the present invention to provide a film thickness measuring method capable of accurately measuring the thickness of an insulator film formed on a surface of a semiconductor substrate.

It is a further object of the present invention to provide a relative dielectric constant measuring method capable of accurately measuring the relative dielectric constant of an insulator film formed on a surface of a semiconductor substrate.

It is another object of the present invention to provide a film thickness measuring apparatus capable of accurately measuring the thickness of an insulator film formed on a surface of a semiconductor substrate.

It is a still further object of the present invention to provide a relative dielectric constant measuring apparatus capable of accurately measuring the relative dielectric constant of an insulator film formed on a surface of a semiconductor substrate.

The present invention provides a thickness measuring method of measuring the thickness of an insulator film formed on one surface of a semiconductor substrate (W), in a non-contact manner with respect to the insulator film. This method comprises: (i) a charging processing step (S2) of charging the insulator film surface in a non-contact manner; (ii) a charge amount measuring step comprising: a step (S1) of obtaining a first flat band voltage by conducting, prior to the charging processing step, a C-V measurement on the semiconductor substrate in a non-contact manner with respect to the insulator film; a step (S3) of obtaining a second flat band voltage by conducting, after the charging processing step, a C-V measurement on the semiconductor substrate in a non-contact manner with respect to the insulator film; and a step (S4) of calculating, based on a difference between the first and second flat band voltages, the charge amount given to the insulator film surface by the charging processing step; (iii) a surface potential measuring step (S5) of measuring, after the charging processing step, the insulator film surface potential in a non-contact manner with respect to the insulator film; and (iv) a step (S8) of calculating the insulator film thickness based on the charge amount measured at the charge amount measuring step and on the surface potential measured at the surface potential measuring step.

The alphabets and numerals in parentheses represent corresponding component elements and the like in embodiments to be discussed later. However, it is not intended that the present invention is construed as limited to these embodiments. This is also applied in the following description.

The insulator film thickness can be obtained when there are known, as to the insulator film, the surface charge amount, the area, the surface potential and the relative dielectric constant. According to the present invention, a charge amount given to the insulator film surface at the charging processing step, is obtained at the charge amount measuring step. If the insulator film surface is not charged before the charging processing step, the charge amount is equal to the entire charge amount of the insulator film surface. The insulator film area is already known in pattern designing. Further, the insulator film surface potential is obtained at the surface potential measuring step. Accordingly, when the relative dielectric constant of the insulator is known, the insulator film thickness can be calculated.

For example, when the insulator film is a gate oxide film made of a silicon oxide, the relative dielectric constant of the insulator film can be regarded as constant independently from the semiconductor substrate to be measured, and is already known. Therefore, by using this known value of relative dielectric constant (e.g., document value), the insulator film thickness can be obtained.

Also, when the rate of change in charge amount with respect to the insulator film surface potential is known instead of the insulator film surface charge amount and the insulator film surface potential, the insulator film thickness can be calculated in a similar manner. By repeating, in a number of times, the charging processing step, the charge amount measuring step and the surface potential measuring step, there are obtained a plurality of data sets each comprising an insulator film surface charge amount and a surface potential. Based on these data, there is obtained the rate of change in charge amount with respect to the insulator film surface potential. In this case, even though the absolute value of the insulator film surface charge amount (all charge amount) cannot accurately be known, the insulator film thickness can accurately be obtained.

According to the present invention, the charging processing step, the charge amount measuring step and the surface potential measuring step are conducted entirely in a non-contact manner. Thus, according to the present invention, the insulator film thickness can be measured in a non-contact manner. More specifically, the semiconductor substrate can be measured in a non-destructive manner. Further, the present invention does not need the step of forming electrodes on an insulator film surface. This does not cause an electric current to leak through the insulator film as done in the case where the measurement is conducted with such electrodes formed. Thus, an accurate measurement can be achieved.

The insulator film surface potential can be measured in a non-contact manner for example with the use of a known Kelvin probe.

The C-V measurement applied to the charge amount measurement, can be conducted with the use of a measuring electrode disposed as separated from the insulator film surface. When the first and second flat band voltages, and the gap (distance) between the insulator film and the measuring electrodes are known, there can be calculated the charge amount given to the insulator film surface by the charging processing. Thus, the charge amount given to the insulator film can be obtained in a non-contact manner. It is noted that this method is not arranged to obtain the charge amount indirectly based on a certain supposition, but is arranged to obtain the charge amount directly. Accordingly, the charge amount thus obtained is accurate.

The charging processing step may comprise a step of charging the insulator film surface by corona discharge (S2).

According to the arrangement above-mentioned, the insulator film surface can uniformly be charged in a non-contact manner by corona discharge. Thus, the insulator film surface charge amount and the insulator film surface potential can be obtained with high precision.

To measure the insulator film thickness, it is required to charge the insulator film surface negatively when the semiconductor substrate is a P-type semiconductor, and positively when the semiconductor substrate is an N-type semiconductor. According to the present invention, the insulator film surface can be charged positively or negatively by selecting the polarity at the time of discharge.

The charging processing step may comprise a step of irradiating, to a semiconductor substrate, ultraviolet rays having a wavelength of not less than 220 nm and not greater than 300 nm.

According to the arrangement above-mentioned, by irradiating ultraviolet rays to the semiconductor substrate, the insulator film can be charged. When the wavelength of the ultraviolet rays is not less than 220 nm and not greater than 300 nm, electrons in the semiconductor substrate can be excited without the semiconductor substrate damaged, and a part of these electrons is moved to the insulator film, causing the insulator film surface to be negatively charged. That is, this method can charge the insulator film surface negatively.

The charging processing step may jointly use corona discharge and irradiation of ultraviolet rays.

The present invention provides a relative dielectric constant measuring method of measuring the relative dielectric constant of an insulator film formed on one surface of a semiconductor substrate (W), in a non-contact manner with respect to the insulator film. This method comprises: (i) a charging processing step (S2) of charging the insulator film surface in a non-contact manner; (ii) a charge amount measuring step comprising: a step (S1) of obtaining a first flat band voltage by conducting, prior to the charging processing step, a C-V measurement on the semiconductor substrate in a non-contact manner with respect to the insulator film; a step (S3) of obtaining a second flat band voltage by conducting, after the charging processing step, a C-V measurement on the semiconductor substrate in a non-contact manner with respect to the insulator film; and a step (S4) of calculating, based on a difference between the first and second flat band voltages, the charge amount given to the insulator film surface by the charging processing step; (iii) a surface potential measuring step (S5) of measuring, after the charging processing step, the insulator film surface potential in a non-contact manner; and (iv) a step (S8) of calculating the insulator film relative dielectric constant based on the charge amount measured at the charge amount measuring step and on the surface potential measured at the surface potential measuring step.

The insulator film relative dielectric constant can be obtained when the surface charge amount, the area, the surface potential and the thickness are known as to the insulator film. According to the present invention, a charge amount given to the insulator film surface at the charging processing step is obtained at the charge amount measuring step. If the insulator film surface is not charged before the charging processing step, the charge amount is equal to the entire charge amount of the insulator film surface. The insulator film area is already known in pattern designing. Further, the insulator film surface potential is obtained at the surface potential measuring step. Accordingly, when the insulator film thickness is known, the insulator film relative dielectric constant can be calculated.

The insulator film thickness can previously be measured by other method. For example, when the insulator film is a general interlayer insulator film, the insulator film thickness is generally large and the relative dielectric constant is generally small. When the insulator film thickness is large, an accurate measured value can be obtained even though the thickness is measured by an optical method. Accordingly, when the thickness of an insulator film to be measured is previously measured with a thickness measuring apparatus of the optical type, the insulator film relative dielectric constant can be calculated with the use of the value thus measured.

According to the present invention, the charging processing step, the charge amount measuring step and the surface potential measuring step are conducted entirely in a non-contact manner. Thus, according to the present invention, the insulator film relative dielectric constant can be measured in a non-contact manner. More specifically, the semiconductor substrate can be measured in a non-destructive manner. Further, the present invention does not need the step of forming electrodes on the insulator film surface. This does not cause an electric current to leak through the insulator film as done in the case where the measurement is conducted with such electrodes formed. Thus, an accurate measurement can be achieved.

The charging processing step may comprise a step (S2) of charging the insulator film surface by corona discharge.

The charging processing step may comprise a step of irradiating, to a semiconductor substrate, ultraviolet rays having a wavelength of not less than 220 nm and not greater than 300 nm.

The present invention provides a thickness measuring apparatus (20, 50) for measuring the thickness of an insulator film formed on one surface of a semiconductor substrate (W), in a non-contact manner with respect to the insulator film. This thickness measuring apparatus comprises: (i) a charging processing unit (1) for charging the insulator film surface in a non-contact manner; (ii) a charge amount measuring unit (2) for measuring, in a non-contact manner with respect to the insulator film, the charge amount given to the insulator film surface by the charging processing unit, this charge amount measuring unit comprising: a contact electrode (5) arranged to come in contact with the other surface of the semiconductor substrate; a measuring electrode (21) arranged to be opposite to, as separated from, the one surface of the semiconductor substrate of which the other surface contacts with the contact electrode; a gap measuring mechanism (27, 28, 29) for measuring the gap between the semiconductor substrate and the measuring electrode; a gap changing mechanism (22, 23) for changing the gap between the semiconductor substrate and the measuring electrode; a bias voltage applying unit (26) for applying a bias voltage between the contact electrode and the measuring electrode, this bias voltage applying unit being capable of changing the magnitude of the bias voltage to be applied; and a capacitance measuring unit (26) for measuring the electric capacitance between the contact electrode and the measuring electrode; and (iii) a surface potential measuring unit (3) for measuring the insulator film surface potential in a non-contact manner with respect to the insulator film.

According to the present invention, the charging processing step of the thickness measuring method is above-mentioned can be executed by the charging processing unit, and the surface potential measuring step of the thickness measuring method above-mentioned can be executed by the surface potential measuring unit.

According to the present invention, the contact electrode is contacted with the other surface of the semiconductor substrate, and the measuring electrode is disposed opposite to, as separated from, the insulator film formed on the one surface of the semiconductor substrate. In this state, the C-V measurement in the thickness measuring method above-mentioned can be executed by measuring the capacitance by the capacitance measuring unit while the bias voltage applying unit applies a bias voltage between the contact electrode and the measuring electrode.

The gap (distance) between the semiconductor substrate and the measuring electrode can be adjusted to a predetermined gap by changing the gap between the semiconductor substrate and the measuring electrode by the gap changing mechanism, while the gap between the semiconductor substrate and the measuring electrode is measured by the gap measuring mechanism. Accordingly, the C-V measurement can be executed with the gap between the semiconductor substrate and the measuring electrode maintained substantially constant before and after the charging processing step. In this case, the charge amount given to the insulator film surface at the charging processing step can be calculated by a simple calculation.

The thickness measuring apparatus may comprise a loader for moving, with respect to the charging processing unit, the charge amount measuring unit and the surface potential measuring unit, a semiconductor substrate on which an insulator film to be measured is formed. The loader may comprise a holding stand for holding a semiconductor substrate. The holding stand may comprise a contact electrode.

The charging processing unit may comprise a corona discharge unit (5, 11) for generating corona discharge on the insulator film surface.

The charging processing unit may comprise an ultraviolet ray irradiation unit (41) for irradiating ultraviolet rays onto the insulator film surface.

The present invention provides a relative dielectric constant measuring apparatus (20, 50) for measuring the relative dielectric constant of an insulator film formed on one surface of a semiconductor substrate (W), in a non-contact manner with respect to the insulator film. This relative dielectric constant measuring apparatus comprises: (i) a charging processing unit (1) for charging the insulator film surface in a non-contact manner; (ii) a charge amount measuring unit (2) for measuring, in a non-contact manner with respect to the insulator film, the charge amount given to the insulator film surface by the charging processing unit, this charge amount measuring unit comprising: a contact electrode (5) arranged to come in contact with the other surface of the semiconductor substrate; a measuring electrode (21) arranged to be opposite to, as separated from, the one surface of the semiconductor substrate of which the other surface contacts with the contact electrode; a gap measuring mechanism (27, 28, 29) for measuring the gap between the semiconductor substrate and the measuring electrode; a gap changing mechanism (22, 23) for changing the gap between the semiconductor substrate and the measuring electrode; a bias voltage applying unit (26) for applying a bias voltage between the contact electrode and the measuring electrode, this bias voltage applying unit being capable of changing the magnitude of the bias voltage to be applied; and a capacitance measuring unit (26) for measuring the electric capacitance between the contact electrode and the measuring electrode; and (iii) a surface potential measuring unit (3) for measuring the insulator film surface potential in a non-contact manner with respect to the insulator film.

This relative dielectric constant measuring apparatus may comprise a loader for moving, with respect to the charging processing unit, the charge amount measuring unit and the surface potential measuring unit, a semiconductor substrate on which an insulator film to be measured is formed. The loader may comprise a holding stand for holding a semiconductor substrate. The holding stand may comprise a contact electrode.

The charging processing unit may comprise a corona discharge unit (5, 11) for generating corona discharge on the insulator film surface.

The charging processing unit may comprise an ultraviolet ray irradiation unit (41) for irradiating ultraviolet rays onto the insulator film surface.

These and other features, objects, advantages and effects of the present invention will be more fully apparent from the following detailed description set forth below when taken in conjunction with the accompanying drawings.

DESCRIPTION OF THE PREFERRED EMBODIMENTS

Figure 1:
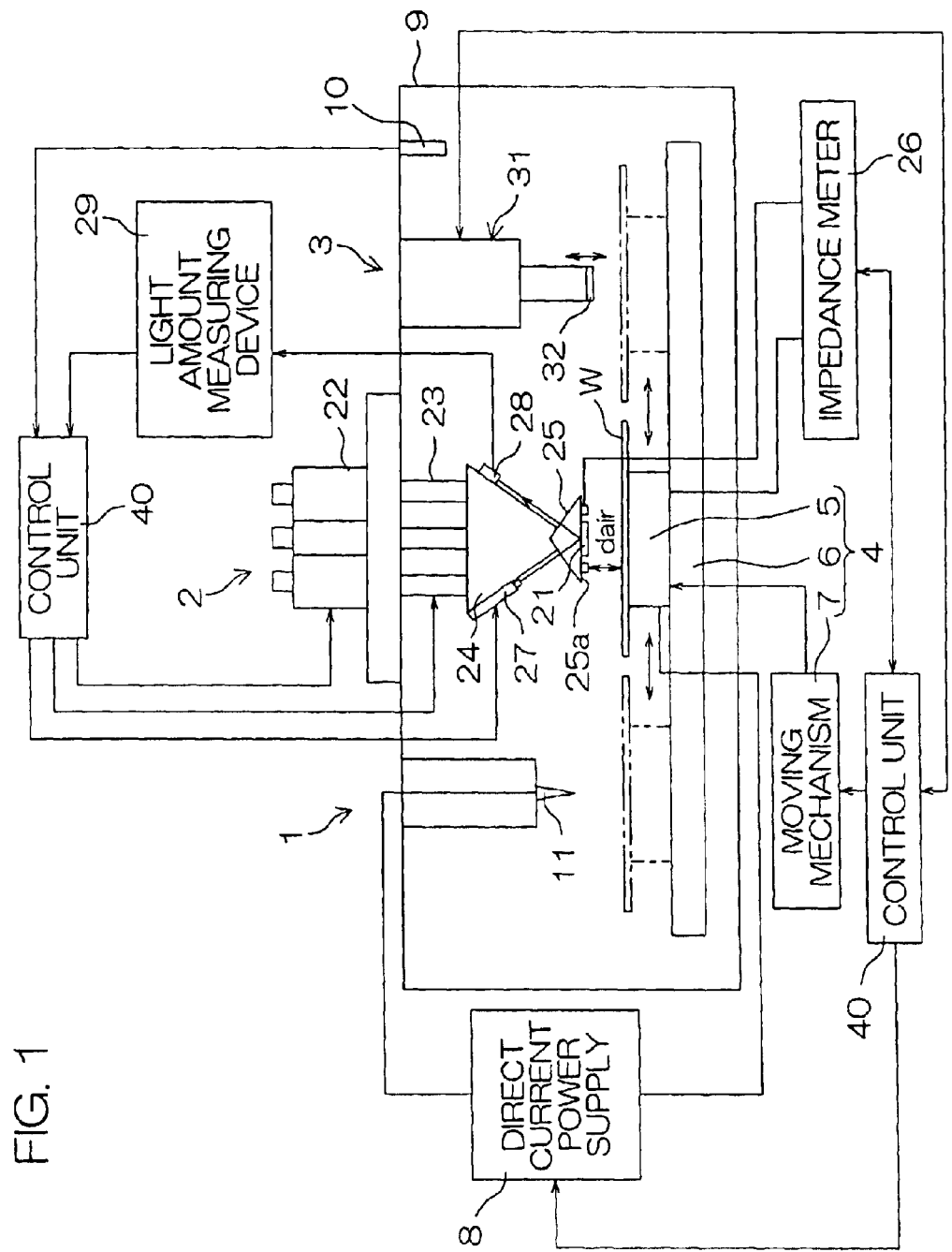
FIG. 1 is a schematic front view of a thickness/relative dielectric constant measuring apparatus according to a first embodiment of the present invention.

FIG. 1 is a schematic front view of a thickness/relative dielectric constant measuring apparatus according to a first embodiment of the present invention.

This thickness/relative dielectric constant measuring apparatus is arranged to measure the thickness or relative dielectric constant of an insulator film formed on a surface of a wafer W as an example of a semiconductor substrate, and comprises a chamber 9. The apparatus further comprises a charging processing unit 1, a charge amount measuring unit 2 and a surface potential measuring unit 3 which are arranged to execute a processing or measurement in the chamber 9. The charging processing unit 1, the charge amount measuring unit 2 and the surface potential measuring unit 3 are successively linearly disposed. The wafer W is arranged to be moved, by a loader 4, among a charging processing position at the charging processing unit 1, a C-V measuring position at the charge amount measuring unit 2, and a surface potential measuring position at the surface potential measuring unit 3.

Disposed in the chamber 9 is a temperature sensor 10 for measuring the ambient temperature in the chamber 9. Provision is made such that an output of the temperature sensor 10 is entered to a control unit 40.

The loader 4 comprises a holding stand 5 for substantially horizontally holding a wafer W, a rail 6 for supporting and linearly guiding the holding stand 5 in a substantially horizontal direction, and a moving mechanism 7 for moving the holding stand 5 along the rail 6. The holding stand 5 is arranged to hold a wafer W for example by vacuum-adsorbing the underside of the wafer W. That portion of the holding stand 5 arranged to come in contact with the wafer W, is made of an electric conductor and serves as a contact electrode.

The charging processing unit 1 is arranged to charge a wafer W by corona discharge, and has a needle 11 for applying a voltage. Each of the needle 11 and the holding stand 5 is connected to a direct current power supply 8. Provision is made such that the wafer W is opposite to the needle 11 at the charging processing position.

Provision is made such that when a wafer W is located in the charging processing position, a direct current voltage is applied between the needle 11 and the holding stand 5 by the direct current power supply 8 to generate corona discharge between the needle 11 and the wafer W, enabling the insulator film on the wafer W surface to be charged. The direct current power supply 8 can reverse the polarity of the voltage to be applied, thus enabling the wafer W to be charged positively or negatively.

The charge amount measuring unit 2 is arranged to conduct a C-V measurement (capacitance-voltage measurement) of a wafer W. The charge amount measuring unit 2 comprises a base 24, a trigonal prism 25 attached to the lower portion of the base 24, and a measuring electrode 21 attached to the bottom face 25a of the prism 25. The prism 25 is substantially horizontally disposed with one of the lateral sides thereof turned down. This side is hereinafter referred to as "the bottom face 25a".

Each of the measuring electrode 21 and the holding stand 5 is connected to an impedance meter 26. Provision is made such that the combined capacitance between the measuring electrode 21 and the holding stand 5 can be measured while applying a bias voltage between the measuring electrode 21 and the holding stand 5. The impedance meter 26 is arranged to change the magnitude of the bias voltage. Thus, a C-V measurement can be made.

The base 24 is connected to a stepping motor 22 through a piezoelectric actuator 23, and is arranged to be vertically moved by the stepping motor 22 and the piezoelectric actuator 23. Provision is made such that the wafer W at the C-V measuring position is opposite to the measuring electrode 21. When the wafer W is located in the C-V measuring position, the gap (distance) between the wafer W and the measuring electrode 21 can be adjusted coarsely by the stepping motor 22, and finely by the piezoelectric actuator 23. The piezoelectric actuator 23 may have a piezoelectric element made of, for example, PZT (lead zirconate titanate).

Attached to the base 24 are a laser oscillator 27 for emitting a laser light and a light receiving sensor 28. Provision is made such that a laser light emitted from the laser oscillator 27 is totally reflected by the bottom face 25a of the prism 25, and received by the light receiving sensor 28. The light receiving sensor 28 is connected to a light amount measuring device 29 for measuring the light amount of the laser light received by the light receiving sensor 28.

The light amount measured by the light amount measuring device 29 is effected by the tunnel effect of the laser light reflected by the bottom face 25a of the prism 25. Accordingly, the gap $d_{air}$ between the wafer W and the measuring electrode 21 can be measured. The principle of this gap measuring method is detailed in Japanese Patent Laid-Open Publication No. H4-132236. Under a certain condition, the logarithm logRt of the transmission factor Rt of the laser light at the bottom face 25a and the gap $d_{air}$ are regarded to be in proportion to each other. When the reflectance is known, the transmission factor Rt can be obtained. Accordingly, when the reflectance is obtained from the light amount of the laser light measured by the light amount measuring device 29, the gap $d_{air}$ can be obtained.

Provision is made such that output signals from the light amount measuring device 29 and the impedance meter 26 are entered into the control unit 40. At the control unit 40, a flat band voltage can be obtained from the C-V measurement result, and the charge amount Q given to the insulator film surface by the charging processing can be obtained from the flat band voltages before and after the charging processing, and from the gap $d_{air}$. A personal computer may be used as the control unit 40.

The surface potential measuring unit 3 has a Kelvin probe 31 having an electrode 32. Provision is made such that the wafer W at the surface potential measuring position is opposite to the Kelvin probe 31.

The Kelvin probe 31 is arranged to vertically vibrate the electrode 32 and to apply a voltage thereto. When the electrode 32 is vibrated at the time a wafer W of which insulator film surface has been charged, is located in the surface potential measuring position, an electric charge undergoing a change based on the vibrational frequency of the electrode 32, is induced to the electrode 32. This electric charge can be negated by applying a suitable voltage to the electrode 32. Based on the voltage at this time, the wafer W surface potential can be obtained. Provision is made such that an output signal of the Kelvin probe 31 is entered to the control unit 40.

The operations of the moving mechanism 7, the direct current power supply 8, the impedance meter 26, the laser oscillator 27 and the Kelvin probe 31 are to be controlled by the control unit 40.

The following description will discuss the steps of measuring the thickness or relative dielectric constant of an insulator film formed on a surface of a wafer W by this thickness/relative dielectric constant measuring apparatus.

Figure 2:
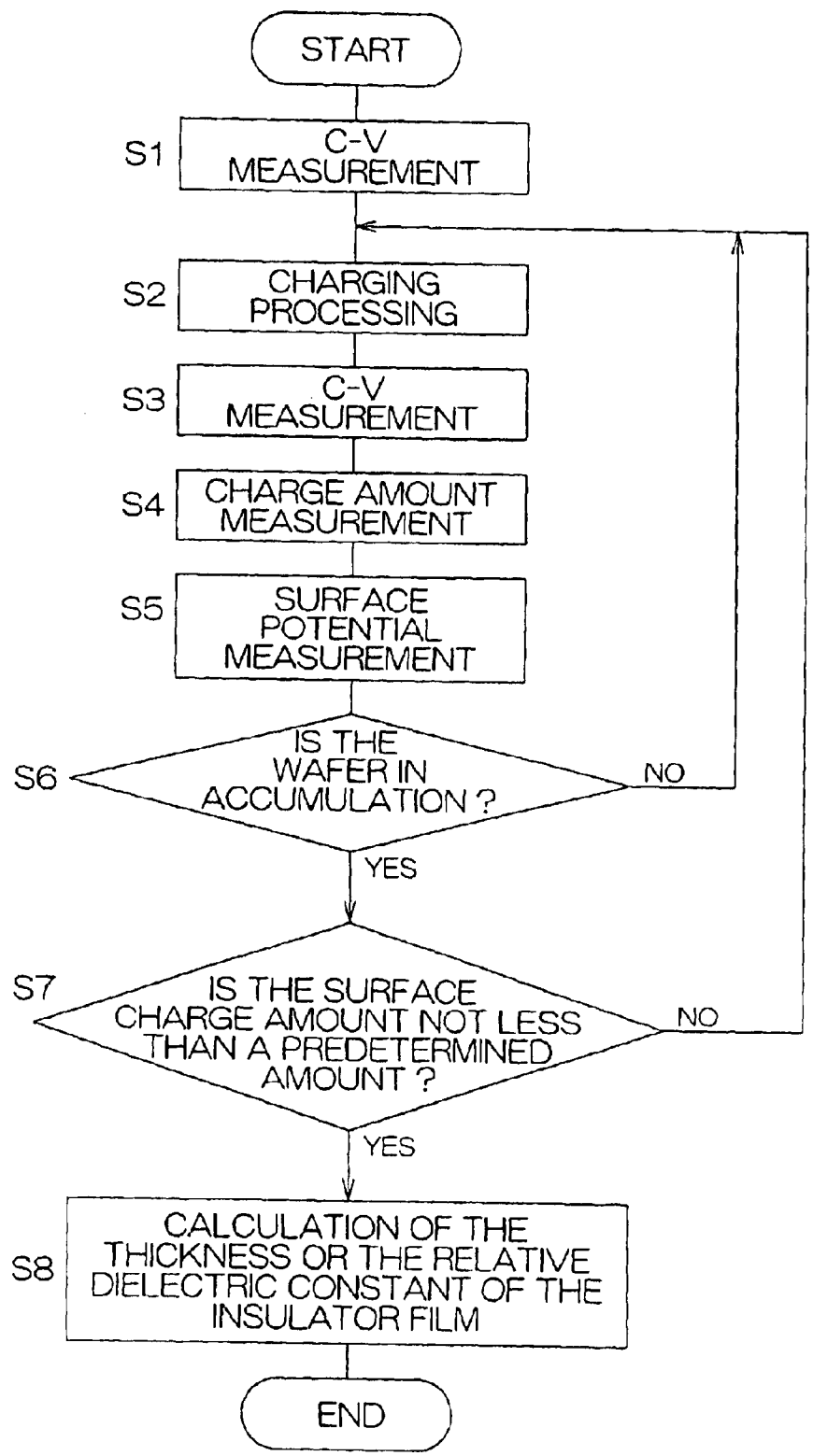
FIG. 2 is a flow chart illustrating the steps of measuring the thickness or relative dielectric constant of an insulator film formed on a surface of a wafer by the thickness/relative dielectric constant measuring apparatus in FIG. 1.

FIG. 2 is a flow chart illustrating the steps of measuring the thickness or relative dielectric constant of an insulator film formed on a surface of a wafer W by the thickness/relative dielectric constant measuring apparatus in FIG. 1. The control unit 40 stores a program for executing measurement based on these steps.

First held on the holding stand 5 is a wafer W with its surface having an insulator film formed thereon being turned up. The control unit 40 controls the moving mechanism 7 to move the wafer W to the C-V measuring position. Then, the control unit 40 operates such that while the gap $d_{air}$ based on the output signal of the light amount measuring device 29 is monitored, the stepping motor 22 and the piezoelectric actuator 23 are controlled to adjust the gap $d_{air}$ to a predetermined value.

Then, the control unit 40 controls the impedance meter 26 to conduct a C-V measurement in which a combined capacitance between the holding stand 5 and the measuring electrode 21 at each bias voltage is measured (Step S1). At this time, the C-V measurement is conducted in a non-contact manner with respect to the wafer W because the wafer W is disposed with a gap provided with respect to the measuring electrode 21. Thus, there is obtained a C-V curve CV1 representing the relationships between bias voltage and combined capacitance.

Figure 3:
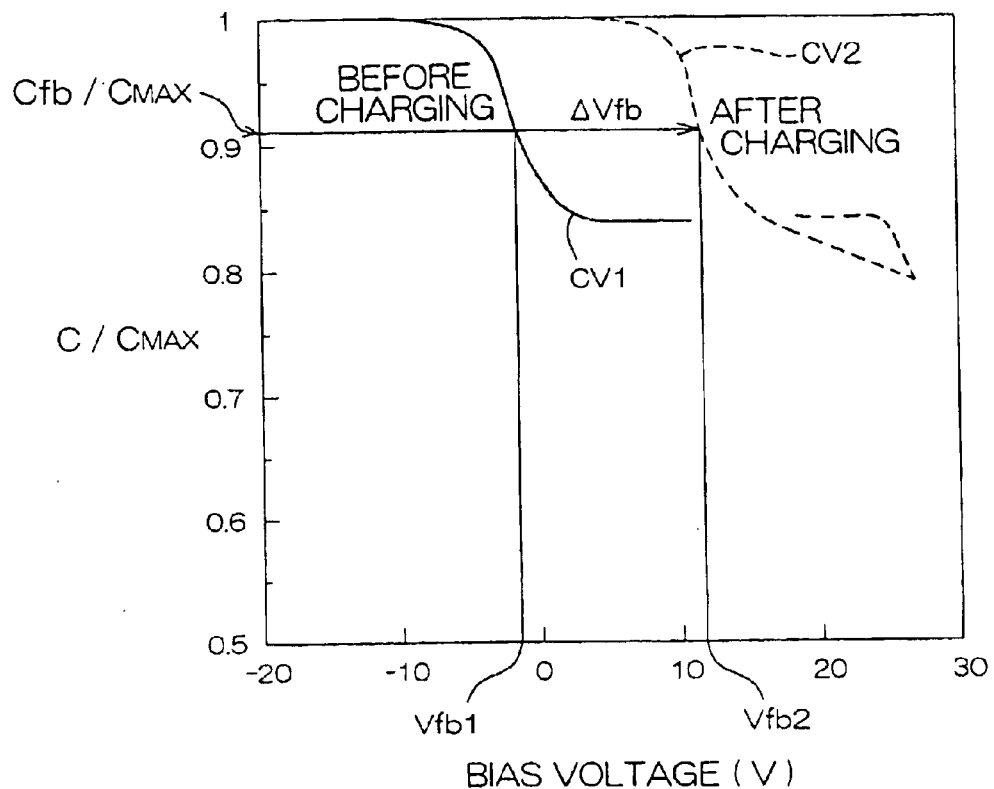
FIG. 3 is a view illustrating an example of a C-V curve.

FIG. 3 shows an example of the C-V curve.

In FIG. 3, the axis of abscissa shows a bias voltage, while the axis of ordinates shows a value obtained by standardizing a combined capacitance C by a maximum combined capacitance $C_{MAX}$ (hereinafter referred to as "a standardized capacitance"). The standardized capacitance $C/C_{MAX}$ converges on 1 in the negative side of the bias voltage. With an increase in bias voltage, the standardized capacitance $C/C_{MAX}$ is reduced, and remarkably reduced at a certain bias voltage. By the operation of the control unit 40, a first flat band voltage Vfb1 is obtained from the C-V curve.

This operation is detailed in the MOS (Metal Oxide Semiconductor) Physics and Technology, P487 (published by WILEY-INTERSCIENCE Company in 1982). First, a flat band capacitance Cfb corresponding to the first flat band voltage Vfb1 is obtained according to the following formula (1):

$$Cfb = Cfbs \, C_{MAX}/(C_{MAX} + Cfbs) \quad (1)$$

wherein Cfbs is the flat band capacitance of silicon (wafer W) and is expressed by the following formula (2):

$$Cfbs = \epsilon_s/\lambda p \quad (2)$$

wherein $\epsilon_s$ is the dielectric constant of the wafer W and is equal to the product of the dielectric constant $\epsilon_0$ in a vacuum and the relative dielectric constant $\epsilon_{si}$ of the wafer W. A document value or the like may be used as the relative dielectric constant $\epsilon_{si}$ of the wafer W. In the formula (2), $\lambda p$ is a Debye length and is expressed by the following formula (3):

$$\lambda p = \{(kT\epsilon_0\epsilon_{si})/(q_o^2 Nd)\}^{1/2} \quad (3)$$

wherein k is a Boltzmann constant, $q_o$ is an elementary charge, T is the temperature of the semiconductor wafer W and may be substituted by the temperature in the chamber 9 measured by the temperature sensor 10, and Nd is the carrier concentration of the wafer W which can be obtained by conducting measurement separately. The carrier concentration Nd is generally measured at the time when the wafer W is purchased. Accordingly, this measured value can also be used. The carrier concentration Nd can also be obtained according to the inclination of the C-V curve.

When the flat band capacitance Cfb is obtained in the manner above-mentioned, the first flat band voltage Vfb1 is obtained as the value of the bias voltage at which the standardized capacitance $C/C_{MAX}$ is equal to $Cfb/C_{MAX}$ in the C-V curve CV1 (See FIG. 3).

Then, the moving mechanism 7 is controlled by the control unit 40 to move the wafer W to the charging processing position. The control unit 40 controls the direct current power supply 8 to apply a predetermined voltage between the needle 11 and the holding stand 5. This generates corona discharge between the needle 11 and the wafer W, causing the insulator film formed on the wafer W surface to be uniformly charged (Step S2).

At this time, the control unit 40 controls the polarity of the direct current power supply 8 based on the information, as to the conduction type of the wafer W, previously given to the control unit 40. That is, the insulator film surface is negatively charged when the wafer W is a P-type semiconductor, and the insulator film surface is positively charged when the wafer W is an N-type semiconductor.

Then, the control unit 40 controls the moving mechanism 7 to move the wafer W to the C-V measuring position where a C-V measurement is conducted (Step S3). At this time, the magnitude of the gap $d_{air}$ is set substantially equal to that at the time of the C-V measurement at Step S1. Thus, a C-V curve CV2 after the charging processing, is obtained (See FIG. 3). The C-V curve CV2 after the charging processing, has a shape as if obtained by shifting, to the positive side of the bias voltage, the C-V curve CV1 before the charging processing.

Then, by the operation of the control unit 40, a flat band voltage (second flat band voltage) Vfb2 after charging processing, is obtained from the C-V curve CV2.

The second flat band voltage Vfb2 is obtained as the value of the bias voltage at which the standardized capacitance $C/C_{MAX}$ is equal to $Cfb/C_{MAX}$ in the C-V curve CV2 (See FIG. 3).

By the operation of the control unit 40, a charge amount Q given to the wafer W surface by the charging processing is obtained, according to the following formula (4), with the use of a difference ΔVfb between the second flat band voltage Vfb2 and the first flat band voltage Vfb1, and of the gap $d_{air}$ (Step S4):

$$\Delta Vfb = -Qd_{air}/\epsilon_0 \quad (4)$$

Then, the control unit 40 controls the moving mechanism 7 to move the wafer W to the surface potential measuring position where the surface potential $V_{surf}$ of the wafer W is measured (Step S5). Thus, there is obtained a set of data comprising the charge amount Q and the surface potential $V_{surf}$ thereat. The C-V measurement (Step S3) and the surface potential $V_{surf}$ measurement (Step S5) are conducted within a period of time during which the charge amount Q of the insulator film surface can be regarded as unchanged.

Then, the control unit 40 judges whether or not the wafer W is in accumulation, i.e., whether or not the combined capacitance C substantially undergoes no change in the vicinity of the zero bias in the C-V curve (Step S6). For example in FIG. 3, the wafer W according to the C-V curve CV1 is not in accumulation, while the wafer W according to the C-V curve CV2 is in accumulation.

When the wafer W is not in accumulation (NO at Step S6), the sequence is returned to Step S2. Then, there are successively conducted a charging processing (Step S2), a C-V measurement (Step S3), a charge amount Q calculation (Step S4), and a surface potential $V_{surf}$ measurement (Step S5). By the charging processing on and after the second time, the insulator film surface is successively greatly charged negatively when the wafer W is a P-type semiconductor, and the insulator film surface is successively greatly charged positively when the wafer W is an N-type semiconductor.

In the charge amount Q calculation (Step S4), the value obtained by the C-V measurement (Step S1) before the first charging processing, is used as the first flat band voltage Vfb1, and the value obtained by the just previous C-V measurement (after the just previous charging processing) is used as the second flat band voltage Vfb2 (This also applied to each charge amount calculation).

Each time Step S2 to Step S5 are executed, there are increased data sets, each comprising a charge amount Q and the surface potential $V_{surf}$ thereat.

When the wafer W is in accumulation (YES at Step S6), it is judged whether or not the charge amount Q is not less than a predetermined amount (Step S7). When the charge amount Q is extremely great, it is always judged that within the range of a bias voltage which can be applied by the impedance meter 26, the wafer W is in accumulation (in which the C-V curves CV1, CV2 in FIG. 3 are being shifted extremely to the positive side of the bias voltage). Accordingly, the flat band voltage cannot be obtained. The predetermined value of the charge amount Q is set such that it can be judged whether or not the flat band voltage of the wafer W can be obtained by a C-V measurement.

When the charge amount Q is smaller than the predetermined value (NO at Step S7), there is a chance that a C-V measurement is further conducted to obtain a flat band voltage. Accordingly, the sequence is returned to Step S2, and there are executed a charging processing (Step S2), a C-V measurement (Step S3), a charge amount Q calculation (Step S4), a surface potential $V_{surf}$ measurement (Step S4) and judgment whether or not the wafer W is in accumulation (Step S6).

When the charge amount Q is not less than the predetermined value (YES at Step S7), the insulator film thickness $t_{ins}$ or relative dielectric constant $\epsilon_{ins}$ is calculated by the control unit 40 (Step S8). The insulator film thickness $t_{ins}$ and relative dielectric constant $\epsilon_{ins}$ are expressed by the following formula (5):

$$dq_u/dV_{surf} = \epsilon_{ins}\epsilon_0/t_{ins} \quad (5)$$

wherein $q_u$ is the charge amount per unit area of the insulator film surface, $\epsilon_0$ is the dielectric constant in a vacuum, and $\epsilon_{ins}$ is the relative dielectric constant of the insulator film. The insulator film area is already known in pattern designing. Accordingly, when the charge amount Q is divided by the insulator film area, the charge amount $q_u$ per unit area is obtained. The value $dq_u/dV_{surf}$ is the rate of change in charge amount $q_u$ per unit area with respect to the surface potential $V_{surf}$ and is equal to the insulator film capacitance $c_{ins}$ per unit area.

Up to this step, there are obtained a plurality of data sets each comprising a charge amount Q and the surface potential $V_{surf}$ thereat.

Figure 4:
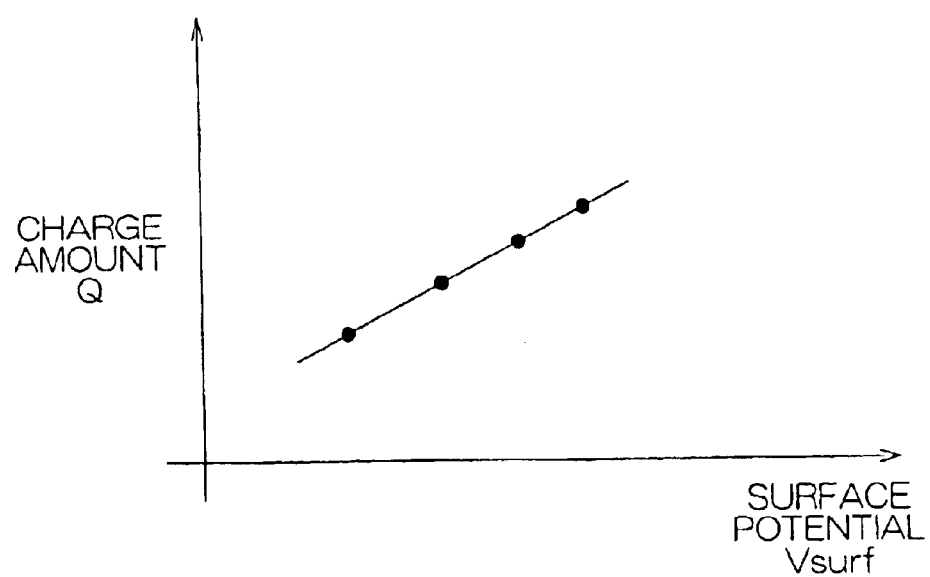
FIG. 4 is a view illustrating the relationship between the surface potential $V_{surf}$ and the charge amount Q.

FIG. 4 is a view illustrating the relationship between the surface potential $V_{surf}$ and the charge amount Q. FIG. 4 shows the relationship in which data of 4 sets are being obtained. When the data of the axis of ordinates are replaced with the charge amounts $q_u$ per unit area, for example the inclination of the regression straight line representing these data becomes $dq_u/dV_{surf}$.

Accordingly, when either one of the insulator film thickness $t_{ins}$ or relative dielectric constant $\epsilon_{ins}$ known, the other can be obtained. For example, when the insulator film is a gate oxide film made of a silicon oxide, the relative dielectric constant $\epsilon_{ins}$ can be regarded as constant independently from the wafer W to be measured, and is already known. Therefore, by using this known value of relative dielectric constant $\epsilon_{ins}$ (e.g., document value), the insulator film thickness $t_{ins}$ can be obtained from the formula (5).

On the other hand, for example when the insulator film is a general interlayer insulator film, the insulator film thickness tins is large and the relative dielectric constant $\epsilon_{ins}$ is small. When the insulator film thickness $t_{ins}$ is large, an accurate measured value can be obtained even though the thickness $t_{ins}$ is measured by an optical method. Accordingly, when the insulator film thickness $t_{ins}$ of a wafer W to be measured is previously measured with a thickness measuring apparatus of the optical type, the relative dielectric constant $\epsilon_{ins}$ can be obtained from the formula (5) with the use of the value thus measured.

The value $dq_u/dV_{surf}$ is preferably obtained only based on the data obtained at the time when the wafer W is in accumulation. In the range of surface potential in which the wafer W is maintained in accumulation, no depletion layer is generated inside of the wafer W. Accordingly, the surface potential $V_{surf}$ and the charge amount Q present on the insulator film surface are in proportional to each other. The proportional coefficient at this time corresponds to the capacitance of the insulator film. Therefore, the proportional coefficient is in proportion to the insulator film relative dielectric constant $\epsilon_{ins}$ and is inversely proportional to the thickness $t_{ins}$. Accordingly, by using $dq_u/dV_{surf}$ obtained only based on the data obtained at the time when the wafer W is in accumulation, the relative dielectric constant $\epsilon_{ins}$ or thickness tins can accurately be obtained.

With the foregoing, measurement of the insulator film thickness $t_{ins}$ or relative dielectric constant $\epsilon_{ins}$ of one wafer W is completed.

In the above measurement of the insulator film thickness $t_{ins}$ or relative dielectric constant $\epsilon_{ins}$, all the C-V measurements (Steps S1 and S3), the charging processing (Step S2), and the surface potential measurement (Step S5) are conducted in a non-contact manner with respect to the insulator film to be measured. That is, the wafer W can be measured in a non-destructive manner. Further, the above measurement does not need the step of forming electrodes on the insulator film faces. This prevents an electric current from leaking through the insulator film as done in the case where the electrodes are formed on the insulator film faces. Thus, an accurate measurement can be achieved.

Further, the charge amount Q itself on the insulator film surface can directly be obtained. Thus, the charge amount Q can accurately be obtained. This results in acquirement of accurate insulator film thickness $t_{ins}$ or relative dielectric constant $\epsilon_{ins}$, thus enabling the semiconductor device process control to be accurately executed.

Figure 5:
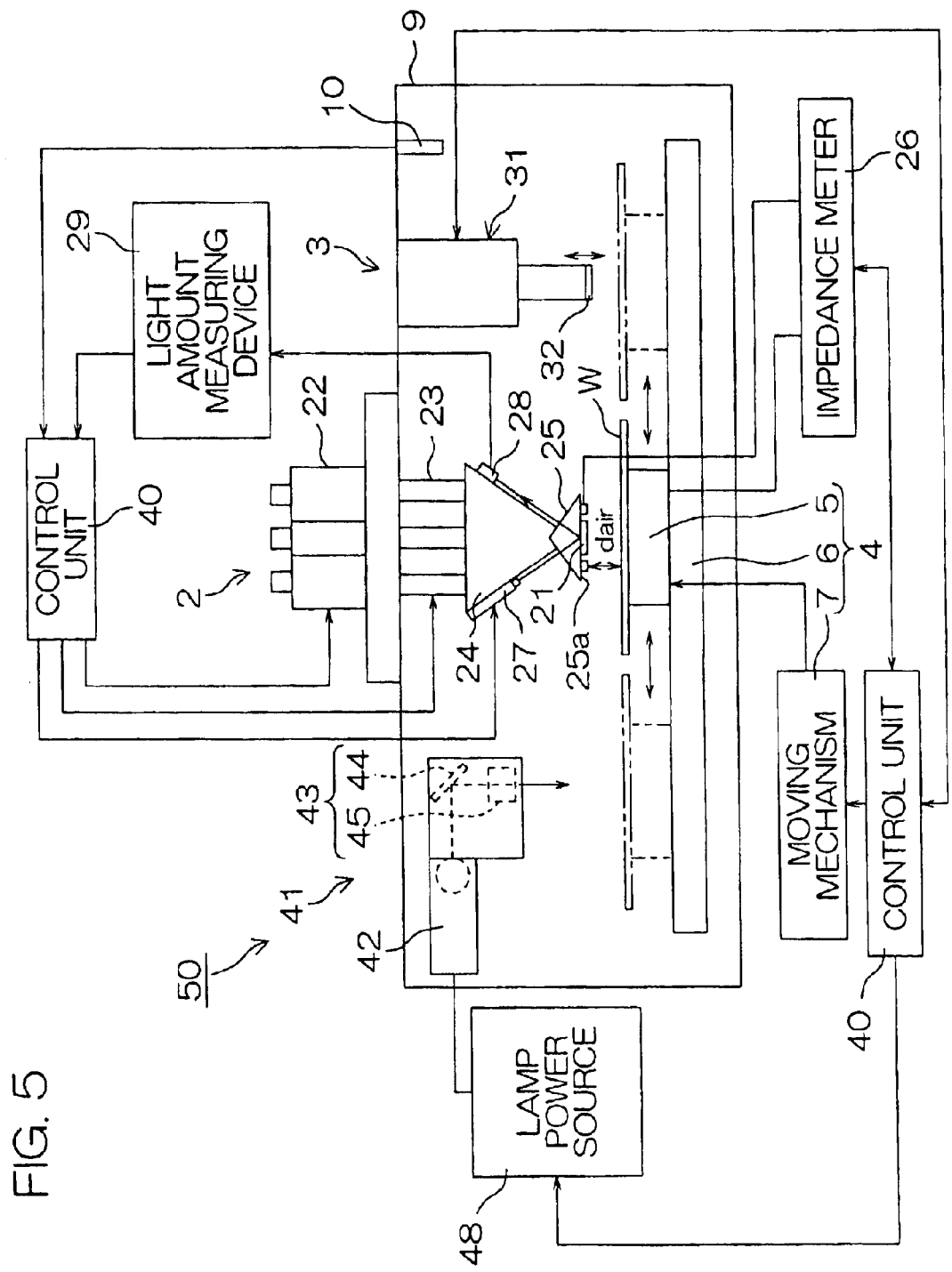
FIG. 5 is a schematic front view of a film thickness/relative dielectric constant measuring apparatus according to a second embodiment of the present invention.

FIG. 5 is a schematic front view of a film thickness/relative dielectric constant measuring apparatus according to a second embodiment of the present invention. In FIG. 5, like parts are generally designated by like reference numerals used in FIG. 1.

This film thickness/relative dielectric constant measuring apparatus 50 comprises, as a charging processing unit, an ultraviolet ray (UV) irradiation unit 41, instead of the charging processing unit 1 having the needle 11 in the film thickness/relative dielectric constant measuring apparatus 20 in FIG. 1. The ultraviolet ray irradiation unit 41 comprises an ultraviolet ray lamp 42 and an optical system 43. The ultraviolet ray lamp 42 is arranged to receive an electric power supplied from a lamp power source 48 and to generate ultraviolet rays having a wavelength of, for example, not less than 220 nm and not greater than 300 nm. The operation of the lamp power source 48 is controlled by a control unit 40.

The optical system 43 comprises a mirror 44 and a lens body 45. The optical system 43 is arranged to direct the traveling direction of the ultraviolet rays generated at the ultraviolet ray lamp 42, toward a wafer W held by a holding stand at a charging processing position under the optical system 43, and is also arranged to irradiate the ultraviolet rays onto a predetermined zone of the wafer W surface. By irradiating the ultraviolet rays onto the wafer W, electrons in the wafer W are excited without the wafer W being damaged, and a part of the electrons is moved to the insulator film, causing the insulator film surface to be negatively charged.

In the wavelength band of 220 nm to 300 nm, the hole in the wafer W is not excited. Accordingly, the insulator film surface is not positively charged. More specifically, the charging processing by this ultraviolet ray irradiation unit 41 can be applied for charging the insulator film surface negatively. Further, the charging processing by the ultraviolet ray irradiation unit 41 can suitably be applied when the insulator film thickness is sufficiently thin (e.g., not greater than 100 nm).

With the use of the film thickness/relative dielectric constant measuring apparatus 50, the film thickness or the relative dielectric constant of an insulator film formed on a surface of the wafer W can be measured according to procedure similar to that applied when the film thickness/relative dielectric constant measuring apparatus 20 in FIG. 1 is used. However, it is noted that the charging processing (Step S2 in FIG. 2) is carried out by irradiating ultraviolet rays onto the wafer W surface by the ultraviolet ray irradiation unit 41.

At this time, there is uniformly charged only that predetermined zone (e.g., a circular zone having a diameter of about 20 mm) on the wafer W surface onto which ultraviolet rays are irradiated. Accordingly, it is required to conduct, on this charged zone, a C-V measurement (Step S3 in FIG. 2) and a surface potential measurement (Step S5 in FIG. 2).

As discussed in the foregoing, when the film thickness/relative dielectric constant measuring apparatus 50 is used, the film thickness or relative dielectric constant can be measured by charging, out of the wafer W surface, only a predetermined zone, which is a measuring object.

When it is required to conduct, on an optional zone on the wafer W surface, measurement of the film thickness or the relative dielectric constant, it is enough to dispose a moving mechanism for relatively moving, in the in-plane direction of the wafer W, at least one of the ultraviolet ray irradiation unit 41 and the holding stand 5 with respect to each other, such that the ultraviolet ray irradiation zone can be adjusted to an optional position of the wafer W held by the holding stand 5. In such a case, the film thickness or relative dielectric constant can also be measured with the wafer W surface charged at its entirety by irradiating ultraviolet rays onto the wafer W surface while moving the ultraviolet ray irradiation zone on the wafer W surface.

The present invention should not be limited to the embodiments above-mentioned. For example, the optical system 43 in the film thickness/relative dielectric constant measuring apparatus 50 of the second embodiment, maybe modified such that ultraviolet rays are irradiated simultaneously onto the whole surface of the wafer W. According to such an arrangement, the wafer W surface can uniformly be charged negatively at its entirety.

A variety of other modifications can be made of the present invention within the scope of the appended claims.

Embodiments of the present invention have been discussed in detail, but these embodiments are mere specific examples for clarifying the technical contents of the present invention. Therefore, the present invention should not be construed as limited to these specific examples. The spirit and scope of the present invention are limited only by the appended claims.

This Application corresponds to Japanese Patent Application Serial No. 2002-212884 filed on Jul. 22, 2002 and Japanese Patent Application No. 2003-171087 filed on Jun. 16, 2003 with Japanese Patent Office, the disclosure of which is incorporated herein by reference.

What we claim is:

1. A method of measuring the relative dielectric constant of an insulator film formed on one surface of a semiconductor substrate, in a non-contact manner with respect to the insulator film, comprising:

a charging processing step of charging the insulator film surface in a non-contact manner;

a charge amount measuring step comprising: a step of obtaining a first flat band voltage by conducting, prior to the charging processing step, a C-V measurement on the semiconductor substrate in a non-contact maimer with respect to the insulator film; a step of obtaining a second flat band voltage by conducting, after the charging processing step, a C-V measurement on the semiconductor substrate in a non-contact manner with respect to the insulator film; and a step of calculating, based on a difference between the first and second flat band voltages, the charge amount given to the insulator film surface by the charging processing step;

a surface potential measuring step of measuring, after the charging processing step, the insulator film surface potential in a non-contact manner with respect to the insulator film; and a step of calculating the insulator film relative dielectric constant based on the charge amount measured at the charge amount measuring step and on the surface potential measured at the surface potential measuring step.

2. A relative dielectric constant measuring method according to claim 1, wherein the charging processing step comprises a step of charging the insulator film surface by corona discharge.

3. A relative dielectric constant insuring method according to claim 1, wherein the charging processing step comprises a step of irradiating, onto the semiconductor substrate, ultraviolet rays having a wavelength of not less than 220 nm and not greater than 300 nm.

4. A relative dielectric constant measuring method according to claim 1, wherein the charging processing step, the charge amount measuring step and the surface potential measuring step are conducted while the semiconductor substrate is held on a same holding stand.

5. A measuring apparatus for measuring the thickness and the relative dielectric constant an insulator film formed on one surface of a semiconductor substrate, in a non-contact manner with respect to the insulator film, comprising:

(i) a charging processing unit for charging the insulator film surface in a non-contact manner;

(ii) a charge amount measuring unit for measuring, in a non-contact manner with respect to the insulator film, the charge amount given to the insulator film surface by the charging processing unit, this charge amount measuring unit comprising:

a contact electrode arranged to come in contact with the other surface of the semiconductor substrate;

a measuring electrode arranged to be opposite to, as separated from, the one surface of the semiconductor substrate of which the other surface contacts with the contact electrode;

a gap measuring mechanism for measuring the gap between the semiconductor substrate and the measuring electrode;

a gap changing mechanism for changing the gap between the semiconductor substrate and the measuring electrode;

a bias voltage applying unit for applying a bias voltage between the contact electrode and the measuring electrode, this bias voltage applying unit being capable of changing the magnitude of the bias voltage to be applied; and a capacitance measuring unit for measuring the electric capacitance between the contact electrode and the measuring electrode;

(iii) a surface potential measuring unit for measuring the insulator film surface potential in a non-contact manner with respect to the insulator film; and (iv) holding stand operable for moving the semiconductor substrate between the charging processing unit, the charge amount measuring unit and the surface potential measuring unit; and (v) a calculating unit arranged to calculate the thickness and the relative dielectric constant of the insulator film based on the charge amount measured by the charge amount measuring unit and the surface potential measured by the surface potential measuring unit, the calculating unit calculating the thickness of the insulator film further based on a known relative dielectric constant of the insulator film, the calculating unit calculating the relative dielectric constant of the insulator film further based on a known thickness of the insulator film.

6. A measuring apparatus according to claim 5, wherein the charging processing unit comprises a corona discharging unit for generating corona discharge on the insulator film surface.

7. A measuring apparatus according to claim 5, wherein the charging processing unit comprises an ultraviolet ray irradiation unit for irradiating ultraviolet rays onto the surface of the insulator film.

8. A relative dielectric constant measuring apparatus for measuring the relative dielectric constant of an insulator film formed on one surface of a semiconductor substrate, in a non-contact manner with respect to the insulator film, comprising:

(i) a charging processing unit for charging the insulator film surface in a non-contact manner;

(ii) a charge amount measuring unit for measuring, in a non-contact manner with respect to the insulator film, the charge amount given to the insulator film surface by the charging processing unit, this charge amount measuring unit comprising:

a contact electrode arranged to come in contact with the other surface of the semiconductor substrate;

a measuring electrode arranged to be opposite to, as separated from, the one surface of the semiconductor substrate of which the other surface contacts with the contact electrode;

a gap measuring mechanism for measuring the gap between the semiconductor substrate and the measuring electrode;

a gap changing mechanism for changing the gap between the semiconductor substrate and the measuring electron;

a bias voltage applying unit for applying a bias voltage between the contact electrode and the measuring electrode, this bias voltage applying unit being capable of changing the magnitude of the bias voltage to be applied; and a capacitance measuring unit for measuring the electric capacitance between the contact electrode and the measuring electrode;

(iii) a surface potential measuring unit for measuring the insulator film surface potential in a non-contact manner with respect to the insulator film; and a calculating unit which calculates the relative dielectric constant of the insulator film based on the charge amount measured in the charge amount measuring unit and on the surface potential measured in the surface potential measuring unit.

9. A relative dielectric constant measuring apparatus according to claim 8, wherein the charging processing unit comprises a corona discharging unit for generating corona discharge on the insulator film surface.

10. A relative dielectric constant measuring apparatus according to claim 8, wherein the charging processing unit comprise an ultraviolet ray irradiation unit for irradiating ultraviolet rays onto the semiconductor substrate.

11. A relative dielectric constant measuring apparatus according to claim 8, further comprising:
a holding stand operable for moving the semiconductor substrate between the charging processing unit, the charge amount measuring unit and the surface potential measuring unit.

* * * * *